United States Patent [19]

Stoltefuss et al.

[11] Patent Number: 5,420,142
[45] Date of Patent: May 30, 1995

[54] CERTAIN 3-FORMYL-1, 4-DIHYDROPYRIDINES AND THEIR PHARMACEUTICAL COMPOSITION AND USE

[75] Inventors: Jürgen Stoltefuss, Haan; Gerhard Franckowiak, Wuppertal; Horst Böshagen, Haan; Martin Bechem, Wuppertal; Rainer Gross, Wuppertal; Siegbert Hebisch, Wuppertal; Joachim Hütter, Leverkusen; Howard-Paul Rounding, Wuppertal; Matthias Schramm, Leverkusen, all of Germany

[73] Assignee: Bayer Aktiengesellschaft, Leverkusen, Germany

[21] Appl. No.: 166,671

[22] Filed: Dec. 14, 1993

Related U.S. Application Data

[63] Continuation of Ser. No. 891,488, May 29, 1992, abandoned.

[30] Foreign Application Priority Data

Jun. 7, 1991 [DE] Germany ............... 41 18 707.5

[51] Int. Cl.$^6$ .................... C07D 401/04; A61K 31/47
[52] U.S. Cl. ..................................... 514/314; 546/167; 546/322
[58] Field of Search ................. 546/167; 514/356, 314

[56] References Cited

U.S. PATENT DOCUMENTS

| | | | |
|---|---|---|---|
| 3,775,422 | 11/1973 | Bossert et al. | 546/118 |
| 4,414,213 | 11/1983 | Poindexter et al. | 546/256 |
| 4,707,479 | 11/1987 | Meyer et al. | 514/222 |
| 5,100,900 | 3/1992 | Stoltefuss et al. | 546/167 |

FOREIGN PATENT DOCUMENTS

| | | |
|---|---|---|
| 0330470 | 2/1989 | European Pat. Off. |
| 0452712 | 3/1991 | European Pat. Off. |
| 3711991 | 4/1987 | Germany |
| 8602640 | 5/1986 | WIPO |

OTHER PUBLICATIONS

Chemical Abstracts, vol. 114, No. 5, 4 Feb. 1991, p. 718.
*Journal of the Chemical Society*, A. I. Meyers, 1986, pp. 920–921.
L. H. Opie, *J. Physiol.*, 1965, pp. 529–541.

*Primary Examiner*—Bernard Dentz
*Attorney, Agent, or Firm*—Sprung Horn Kramer & Woods

[57] ABSTRACT

The present invention relates to the use of 3-formyl-1,4-dihydropyridine derivatives as medicaments for the control of cardiovascular diseases, in particular of pathologically changed blood pressure and of cardiac insufficiency, new compounds and a process for their preparation.

8 Claims, No Drawings

CERTAIN 3-FORMYL-1, 4-DIHYDROPYRIDINES AND THEIR PHARMACEUTICAL COMPOSITION AND USE

This application is a continuation of application Ser. No. 07/891,488, filed May 29, 1992 and now abandoned.

The invention relates to the use of-3-formyl-1,4-dihydropyridine derivatives as medicaments for the control of cardiovascular diseases, in particular of pathologically changed blood pressure and of cardiac insufficiency, new compounds and a process for their preparation.

It is known that 1,4-dihydropyridines having a 3,5-diester, 3,5-diacyl or 3,5-ester/acyl group have a calcium antagonist action [cf. for example German Offenlegungsschrift 3,711,991].

Moreover, N-substituted 1,4-dihydropyridine derivatives having a formyl group in the 3-position are described as chemotherapeutics in EP 330,470.

In the publication [Hons, You Hwa, Suh, Jung Jin, Yuhan Res. Cent., Kunpo 433–810, S. Korea, Yakhak Hoechi, 33(5), 2.90–295], the compound methyl 5-formyl-1,4-dihydro-2,6-dimethyl-4-(3-nitro-phenyl) of pyridine is described without details as a pharmacological action.

The present invention relates to 3-formyl-1,4-dihydropyridines of the general formula (I)

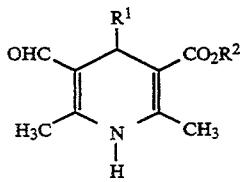

in which $R^1$ represents phenyl which is optionally monosubstituted to trisubstituted by identical or different substituents from the group comprising nitro, cyano, halogen, trifluoromethyl, trifluoromethylthio, trifluoromethoxy and difluoromethoxy or by straight-chain or branched alkyl, alkoxy, alkylthio or alkoxycarbonyl each having up to 8 carbon atoms, or by a group of the formula $-O(CH_2)_n-R^3$, $-S-(CH_2)_n-R^3$ or $-CO-(CH_2)_n-R^3$, in which n denotes a number 0, 1, 2, 3 or 4, $R^3$ denotes aryl having 6 to 10 carbon atoms, which is optionally monosubstituted to trisubstituted by identical or different substituents from the group comprising halogen, nitro, trifluoromethyl, trifluoromethoxy, difluoromethoxy and trifluoromethylthio or by straight-chain or branched alkyl or alkoxy each having up to 8 carbon atoms, or represents a radical of the formula

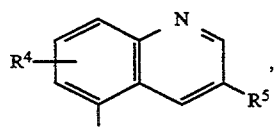

-continued

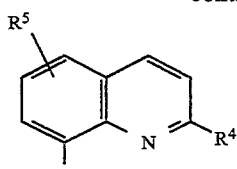

in which $R^4$ denotes hydrogen, halogen or straight-chain or branched alkyl or alkoxy each having up to 8 carbon atoms, $R^5$ denotes phenyl which is optionally monosubstituted or disubstituted by identical or different substituents from the group comprising halogen, nitro, cyano, trifluoromethyl, trifluoromethoxy, trifluoromethylthio, straight-chain or branched alkyl, alkoxy or alkoxycarbonyl each having up to 8 carbon atoms and carboxyl, $R^2$ represents hydrogen, or represents straight-chain or branched alkyl, alkenyl, alkadienyl or alkinyl each having up to 10 carbon atoms, which are optionally monosubstituted or disubstituted by identical or different substituents from the group comprising halogen, hydroxyl, carboxyl, cyano and nitro or by straight-chain or branched alkylthio, alkoxy, alkoxycarbonyl, acyl or acyloxy each having up to 8 carbon atoms or by phenoxy or phenyl, where both the latter can in turn be monosubstituted or disubstituted by identical or different substituents from the group comprising halogen and straight-chain or branched alkyl or alkoxy each having up to 6 carbon atoms, and their physiologically acceptable salts, with the proviso that if $R^1$ represents m-nitrophenyl, $R^2$ must not denote methyl.

Physiologically acceptable salts can be salts of the compounds according to the invention with inorganic or organic acids. Salts with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, benzenesulphonic acid, toluenesulphonic acid or naphthalenedisulphonic acid are preferred.

The compounds according to the invention exist in stereoisomeric forms which either behave as image and mirror image (enantiomers) or which do not behave as image and mirror image (diastereomers). The invention relates both to the antipodes and to the racemic forms and also the diastereomer mixtures. Like the diastereomers, the racemic forms can be separated into the stereoisomerically homogeneous constituents in a known manner (cf. E. L. Eliel, Stereochemistry of Carbon Compounds, McGraw Hill, 1962 ).

Preferred compounds of the general formula (I) are those in which $R^1$ represents phenyl which is optionally monosubstituted or disubstituted by identical or different substituents from the group comprising nitro, cyano, fluorine, chlorine, trifluoromethyl, trifluoromethoxy and difluoromethoxy, or by straight-chain or branched alkyl, alkoxy, alkylthio or alkoxycarbonyl each having up to 6 carbon atoms, or by a group of the formula —O(CH$_2$)$_n$—R$^3$, —S(CH$_2$)$_n$—R$^3$ or —CO(CH$_2$)$_n$—R$^3$,
in which
n denotes a number 0, 1 or 2,
and
R$^3$ denotes phenyl which is optionally monosubstituted or disubstituted by identical or different substituents from the group comprising nitro, fluorine, chlorine, trifluoromethyl, trifluoromethoxy and difluoromethoxy or by straight-chain or branched alkyl or alkoxy each having up to 6 carbon atoms,
or represents a radical of the formula

[structure: quinoline with R$^4$ and R$^5$ substituents]

or

[structure: quinoline with R$^4$ and R$^5$ substituents]

in which
R$^4$ denotes hydrogen,
R$^5$ denotes phenyl which is optionally substituted by fluorine, chlorine, nitro, cyano or trifluoromethyl or by straight-chain or branched alkyl or alkoxy each having up to 6 carbon atoms,
R$^2$ represents hydrogen or straight-chain or branched alkyl or alkenyl each having up to 8 carbon atoms, which are optionally substituted by fluorine, chlorine, hydroxyl, carboxyl, cyano or nitro or by straight-chain or branched alkylthio, alkoxy, alkoxycarbonyl, acyl or acyloxy each having up to 6 carbon atoms or by phenoxy or phenyl,
with the proviso that if R$^1$ represents m-nitrophenyl, R$^2$ must not denote methyl.

Particularly preferred compounds of the general formula (I) are those
in which
R$^1$ represents phenyl which is optionally substituted by nitro, fluorine, chlorine, bromine, trifluoromethyl, trifluoromethoxy or difluoromethoxy, by straight-chain or branched alkyl or alkoxy each having up to 4 carbon atoms or by a group of the formula —O(CH$_2$)$_n$—R$^3$ or —S(CH$_2$)$_n$—R$^3$,
in which
n denotes the number 1
R$^3$ denotes phenyl which is optionally substituted by nitro, fluorine, chlorine or trifluoromethoxy or by straight-chain or branched alkyl or alkoxy each having up to 4 carbon atoms,
or represents a radical of the formula

[structure: quinoline with R$^4$ and R$^5$ substituents]

in which
R$^4$ denotes hydrogen,
R$^5$ denotes phenyl which is optionally substituted by fluorine, chlorine, nitro or trifluoromethyl or by straight-chain or branched alkyl or alkoxy each having up to 4 carbon atoms,
R$^2$ represents hydrogen, or straight-chain or branched alkyl having up to 6 carbon atoms, which is optionally substituted by hydroxyl, carboxyl or cyano or by straight-chain or branched alkoxycarbonyl, alkoxy or acyloxy each having up to 4 carbon atoms,
with the proviso that if R$^1$ represents m-nitrophenyl, R$^2$ must not denote methyl.

Moreover, a process for the preparation of the compounds of the general formula (I) according to the invention has been found, characterised in that activated compounds of the general formula (II)

[structure (II): dihydropyridine with R$^1$, CO$_2$R$^2$, X, H$_3$C, CH$_3$, NH]

in which
R$^1$ and R$^2$ have the abovementioned meaning,
and
X represents an activating radical of the formula

[structures: —CO—N(pyrrole-like) or —C(CH$_3$)$_2$—O—N]

are either reduced directly or after a prior alkylation step, in inert organic solvents at temperatures of 0°–100° C.

The process according to the invention can be illustrated by way of example by the following equation:

[structure: dihydropyridine with quinoline-phenyl substituent, H$_5$C$_2$O$_2$C, CO—N(pyrrole), H$_3$C, CH$_3$, NH]

$\xrightarrow{\text{NaBH}_4}{\text{Tetrahydrofuran}}$

[structure: dihydropyridine with quinoline-phenyl substituent, H$_5$C$_2$O$_2$C, CHO, H$_3$C, CH$_3$, NH]

Suitable solvents for the process are all the inert organic solvents. These preferably include alcohols such as methanol, ethanol, n- or isopropanol, ethers such as diethyl ether, tetrahydrofuran, dioxane or glycol monomethyl ether or glycol dimethyl ether, glacial acetic acid, pyridine, dianethylformamide, dimethyl sulphoxide, acetonitrile or hexamethylphosphoric triamide or acetonitrile.

The reduction is in general carried out using hydrides such as, for example, sodium borohydride, lithium aluminium hydride or diisobutylaluminium hydride. Sodium borohydride is preferred.

The reducing agent is in general employed in an amount from 0.5 to 10 mol, preferably from 1 mol to 3 mol, relative to 1 mol of the compounds of the general formula (II).

The reduction is in general carried out in a temperature range from 0° C. to 100° C., preferably from 25° C. to 60° C.

The reduction can in general be carried out at normal pressure, elevated pressure or reduced pressure (for example from 0.5 to 5 bar), but preferably at normal pressure.

The alkylation is carried out in the abovementioned solvents at temperatures from 0° C. to +150° C., preferably at room temperature to +100° C. at normal pressure.

Alkylating agents which can be employed in the process are, for example, ($C_1$–$C_8$)-alkyl halides, sulphonic acid esters or substituted or unsubstituted ($C_1$–$C_6$)-dialkyl or ($C_1$–$C_6$)-diaryl sulphates, preferably methyl iodide, p-toluenesulphonic acid esters or dimethyl sulphate.

The above preparation processes are only given for illustration. The preparation of the compounds of the formula (I) is not restricted to these processes, but any modification of these processes can be used in the same manner for the preparation of the compounds according to the invention.

The compounds of the general formula (II) are known in some cases or can be prepared by known methods [cf. U.S. Pat. No. 4,707,479].

The compounds of the general formula (1) according to the invention exhibit an unforeseeable, useful pharmacological spectrum of action. They influence the contractility of the heart and the tone of the smooth musculature. They can therefore be employed in medicaments for influencing pathologically changed blood pressure, as coronary therapeutics and for the treatment of cardiac insufficiency. Moreover, they can be used for the treatment of cardiac arrhythmias, for the reduction of blood sugar, for the detumescence of mucosa and for influencing the salt and liquid balance.

The cardiac and vascular effects were found on isolated perfused guinea pig hearts. To this end, the hearts of guinea pigs of 250 to 350 g weight are used. The animals are killed by a blow to the head, the thorax is opened, and a metal cannula is tied into the exposed aorta. The heart is separated out of the thorax with the lungs and connected to the perfusion apparatus via an aortic cannula with continuous perfusion. The lungs are separated at the roots of the lung. The perfusion medium used is a Krebs-Henseleit solution (1) (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), the $CaCl_2$ content of which is 1.2 mmol/l. 10 mmol/l of glucose are added as an energy-producing substrate. The solution is filtered free from particles before perfusion. The solution is aerated with carbogen (95% $O_2$, 5% $CO_2$) to maintain the pH 7.4. The hearts are perfused with a constant flow (10 ml/min) at 32° C. by means of a peristaltic pump.

For the measurement of cardiac function, a liquid-filled latex balloon which is connected to a pressure transducer via a liquid column is inserted into the left ventricle through the left auricle, and the isovolumetric contractions are recorded on a rapid recorder (Opie, L., J. Physiol., 180 (1965), 529–541). The perfusion pressure is recorded by means of a pressure transducer which is connected to the perfusion system upstream of the heart. Under these conditions, a reduction in the perfusion pressure indicates a coronary dilation, and an increase or decrease in the left-ventricular contraction amplitude indicates a reduction or an increase in the heart contractility. The compounds according to the invention are perfused into the perfusion system in suitable dilutions just upstream of the isolated heart.

Substance effects on the contraction amplitude of isolated guinea pig heart auricles at an active compound concentration of $10^{-4}$ g/l.

| Ex. No. | Contractility (% control) |
|---|---|
| 1 | +32 |
| 3 | +31 |
| 4 | +41 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to attain the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may sometimes be necessary to deviate from the amounts mentioned, in particular depending on the body weight and on the type of administration routes, on individual behaviour towards the medicament, the nature of its formulation and the time or interval at which administration takes place. Thus, in some cases it may be sufficient to manage with less than the minimum amount previously mentioned, while in other cases the upper limit mentioned must be exceeded. In the case of the administration of larger amounts, it may be necessary to divide these into several individual doses over the course of the day.

STARTING COMPOUNDS
EXAMPLE 1

Methyl 1,4-dihydro-2,6-dimethyl-4-(2-trifluoromethylphenyl)-3-(4,4-dimethyl-oxazolin-2-yl)-pyridine-5-carboxylate

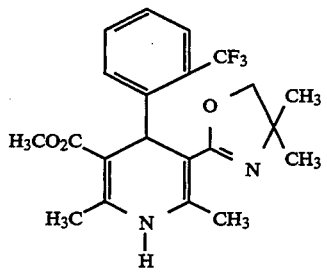

17.4 g (0.1 mol) of o-trifluoromethylbenzaldehyde, 15.5 g (0.1 mol) of 2-acetonyl-4,4-dimethyloxazoline and 11.5 g (0.1 mol) of methyl β-aminocrotonate are heated under reflux in 150 ml of i-propanol for 12 h. The solvent is then removed in vacuo and the residue is separated on a silica gel column. 18 g of the title compound are obtained. m.p.: 181° C.

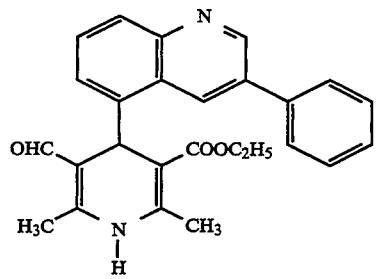

1 g (2.1 mol) of ethyl 1,4-dihydro-2,6-dimethyl-4-(3-phenyl-quinolin-5-yl)-pyridine-3-carboxylate-5-carboxylic acid imidazolide are dissolved in 50 ml of dry tetrahydrofuran and treated with 500 mg (12.6 mmol) of sodium borohydride. The mixture is stirred at 60° C. for 20 hours, concentrated, dissolved in ethyl acetate and washed with water. The ethyl acetate phase is dried and concentrated. The product mixture is purified on a silica gel column using toluene/ethyl acetate mixture. 146 mg of a colourless substance of melting point 275°–277° C. are obtained.

The examples listed in Table 1 are prepared in analogy to the procedure of Example 1:

TABLE 1

| Ex. No. | R¹ | R² | m.p. °C. |
|---|---|---|---|
| 2 | 2-(3-methoxybenzyloxy)phenyl | —CH₃ | 186–188 |
| 3 | 3-phenylquinolin-5-yl | —CH(CH₃)₂ | 261 |
| 4 | 3-phenylquinolin-5-yl | —CH₃ | 282 |
| 5 | 2-trifluoromethylphenyl | —CH₃ | |

PREPARATION EXAMPLES
EXAMPLE 1

Ethyl 1,4-dihydro-2,6-dimethyl-3-formyl-4-(3-phenylquinolin-5-yl)-pyridine-5-carboxylate

We claim:
1. A 3-formyl-1-,4-dihydropyridine of the formula

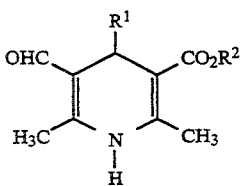

in which

R₁ represents a radical of the formula

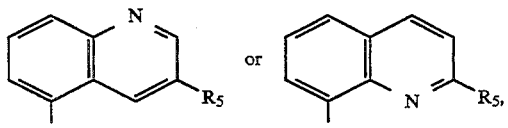

R₅ denotes phenyl which is optionally substituted by fluorine, chlorine, nitro, cyano or trifluoromethyl or by straight-chain or branched alkyl or alkoxy each having up to 6 carbon atoms, and R₂ represents hydrogen or straight-chain or branched alkyl or alkenyl each having up to 8 carbon atoms, which are optionally substituted by fluorine, chlorine, hydroxyl, carboxyl, cyano and nitro or by straight-chain or branched alkylthio, alkoxy, alkoxycarbonyl, acyl or acyloxy each having up to 6 carbon atoms or by phenoxy or phenyl.

2. A compound or salt thereof according to claim 1, in which

R₂ represents hydrogen, or straight chain or branched alkyl having 2 to 6 carbon atoms, which is optionally substituted by hydroxyl, carboxyl or cyano or by straight-chain or branched alkoxycarbonyl, alkoxy or acyloxy each having up to 4 carbon atoms.

3. A compound according to claim 1, wherein such compound is ethyl 1,4-dihydro-2,6-dimethyl-3-formyl-4-(3-phenylquinolin-5-yl)-pyridine-5-carboxylate of the formula

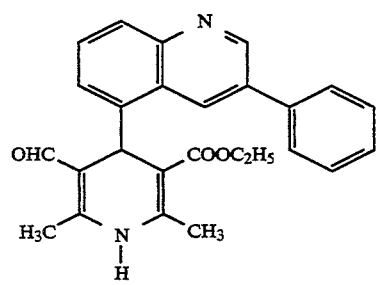

4. A compound according to claim 1, wherein such compound is isopropyl 1,4-dihydro-2,6-dimethyl-3-formyl-4-(3-phenylquinolin-5-yl )-pyridine-5-carboxylate of the formula

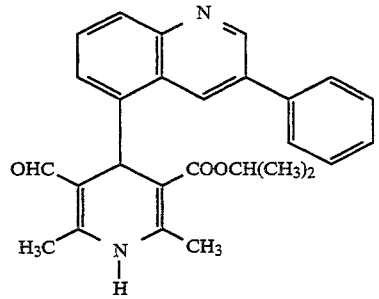

5. A compound according to claim 1, wherein such compound is methyl 1,4-dihydro-2,6-dimethyl-3-formyl-4-(3-phenylquinolin-5-yl)-pyridine-5-carboxylate of the formula

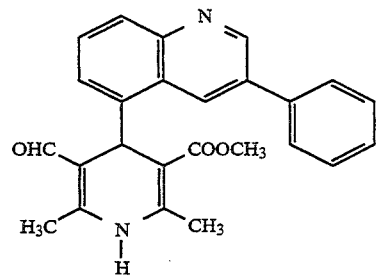

6. A cardioactive composition comprising a cardioactively effective amount of a compound or salt thereof according to claim 1 and a pharmacologically acceptable diluent.

7. A method of treating a patient suffering from a cardiovascular condition which requires an increase in contractility of the heart, which comprises administering to such patient an amount effective therefor of a 3-formyl-1,1,4-dihydropyridine of the formula

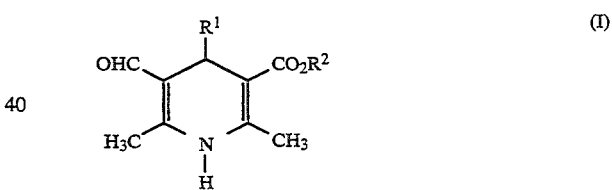

or pharmaceutically acceptable salt thereof, in which

R¹ represents a radical of the formula

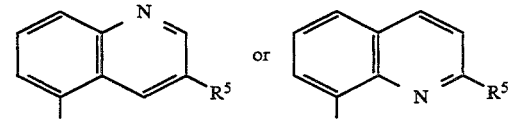

R⁵ denotes phenyl which is optionally substituted by fluorine, chlorine, nitro, cyano or trifluoromethyl or by straight-chain or branched alkyl or alkoxy each having up to 6 carbon atoms, and R² represents hydrogen or straight-chain or branched alkyl or alkenyl each having up to 8 carbon atoms, which are optionally substituted by fluorine, chlorine, hydroxyl, carboxyl, cyano and nitro or by straight-chain or branched alkylthio, alkoxy, alkoxycarbonyl, acyl or acyloaxy each having up to 6 carbon atoms or by phenoxy or phenyl.

8. The method according to claim 7, wherein the compound is ethyl 1,4-dihydro-2,6-dimethyl-3-formyl-4-(3-phenylquinolin-5-yl)-pyridine-5-carboxylate,
isopropyl 1,4-dihydro-2,6-dimethyl-3-formyl-4-(3-phenylquinolin-5-yl)-pyridine-5-carboxylate, or
methyl 1,4-dihydro-2,6-dimethyl-3-formyl-4-(3-phenylquinolin-5-yl)-pyridine-5-carboxylate.

* * * * *